(12) United States Patent
Cummins et al.

(10) Patent No.: US 7,850,709 B2
(45) Date of Patent: Dec. 14, 2010

(54) BLOOD VESSEL CLOSURE CLIP AND DELIVERY DEVICE

(75) Inventors: Christy Cummins, Naas (IE); Robert Stevenson, Clontarf (IE)

(73) Assignee: Abbott Vascular Inc., Santa Clara, CA (US)

( * ) Notice: Subject to any disclaimer, the term of this patent is extended or adjusted under 35 U.S.C. 154(b) by 517 days.

(21) Appl. No.: 10/517,004

(22) PCT Filed: Jun. 4, 2003

(86) PCT No.: PCT/IE03/00088

§ 371 (c)(1),
(2), (4) Date: Jun. 6, 2005

(87) PCT Pub. No.: WO03/101310

PCT Pub. Date: Dec. 11, 2003

(65) Prior Publication Data

US 2005/0234508 A1      Oct. 20, 2005

(30) Foreign Application Priority Data

Jun. 4, 2002    (IE)    ................ S2002/0451

(51) Int. Cl.
*A61B 17/08* (2006.01)
(52) U.S. Cl. ...................... 606/213; 606/153
(58) Field of Classification Search ............ 606/151, 606/153, 213, 219, 232, 157, 158; 623/1.11, 623/1.36
See application file for complete search history.

(56) References Cited

U.S. PATENT DOCUMENTS

| | | |
|---|---|---|
| 287,046 A | 10/1883 | Norton |
| 438,400 A | 10/1890 | Brennen |
| 1,088,393 A | 2/1914 | Backus |
| 1,331,401 A | 2/1920 | Summers |
| 1,426,111 A | 8/1922 | Sacker |
| 1,516,990 A | 11/1924 | Silverman |
| 1,596,004 A | 8/1926 | De Bengoa |
| 1,647,958 A | 11/1927 | Ciarlante |
| 1,847,347 A | 3/1932 | Maisto |
| 1,852,098 A | 4/1932 | Anderson |
| 1,880,569 A | 10/1932 | Weis |
| 2,075,508 A | 3/1937 | Davidson |

(Continued)

FOREIGN PATENT DOCUMENTS

CA    2 339 060    2/2000

(Continued)

OTHER PUBLICATIONS

Database WPI; Section PQ, Week 200120; Derwent Publications Ltd., London GB; AN 2001-203165; XP002199926 & ZA 200 100 528 A (Anthony T), Feb. 28, 2001 abstract.

(Continued)

*Primary Examiner*—Julian W Woo
(74) *Attorney, Agent, or Firm*—Workman Nydegger

(57) ABSTRACT

A clip for closing a puncture hole in a blood vessel comprises a ring 12 having a resiliently expandable circumference and a plurality of barbed prongs 14 extending at least approximately in the same direction from one edge of the ring. A device for deploying such a clip is also described.

8 Claims, 5 Drawing Sheets

U.S. PATENT DOCUMENTS

| | | |
|---|---|---|
| 2,087,074 A | 7/1937 | Tucker |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,664,345 A | 5/1972 | Dabbs et al. |
| 3,677,243 A | 7/1972 | Nerz |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,976,079 A | 8/1976 | Samuels et al. |
| 3,985,138 A | 10/1976 | Jarvik |
| 4,014,492 A | 3/1977 | Rothfuss |
| 4,018,228 A | 4/1977 | Goosen |
| 4,064,881 A | 12/1977 | Meredith |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,917,087 A | 4/1990 | Walsh et al. |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,997,439 A | 3/1991 | Chen |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,147,381 A | 9/1992 | Heimerl et al. |

| Patent Number | Kind | Date | Inventor(s) |
|---|---|---|---|
| 5,156,609 | A | 10/1992 | Nakao et al. |
| 5,158,566 | A | 10/1992 | Pianetti |
| 5,167,634 | A | 12/1992 | Corrigan, Jr. et al. |
| 5,167,643 | A | 12/1992 | Lynn |
| 5,171,249 | A | 12/1992 | Stefanchik et al. |
| 5,171,250 | A | 12/1992 | Yoon |
| 5,171,251 | A | 12/1992 | Bregen et al. |
| 5,176,648 | A | 1/1993 | Holmes et al. |
| 5,176,682 | A | 1/1993 | Chow |
| 5,192,288 | A | 3/1993 | Thompson et al. |
| 5,192,300 | A | 3/1993 | Fowler |
| 5,192,301 | A | 3/1993 | Kamiya et al. |
| 5,192,302 | A | 3/1993 | Kensey et al. |
| 5,192,602 | A | 3/1993 | Spencer, deceased et al. |
| 5,203,787 | A | 4/1993 | Noblitt et al. |
| 5,209,756 | A | 5/1993 | Seedhorm et al. |
| 5,217,024 | A | 6/1993 | Dorsey et al. |
| 5,219,359 | A | 6/1993 | McQuilkin et al. |
| 5,222,974 | A | 6/1993 | Kensey et al. |
| 5,226,908 | A | 7/1993 | Yoon |
| 5,234,449 | A | 8/1993 | Bruker et al. |
| 5,236,435 | A | 8/1993 | Sewell, Jr. |
| 5,236,445 | A | 8/1993 | Hayhurst et al. |
| 5,242,457 | A | 9/1993 | Akopov et al. |
| 5,242,459 | A | 9/1993 | Buelna |
| 5,246,156 | A | 9/1993 | Rothfuss et al. |
| 5,246,443 | A | 9/1993 | Mai |
| 5,250,058 | A | 10/1993 | Miller et al. |
| 5,254,105 | A | 10/1993 | Haaga |
| 5,258,015 | A | 11/1993 | Li et al. |
| 5,269,792 | A | 12/1993 | Kovac et al. |
| 5,275,616 | A | 1/1994 | Fowler |
| 5,282,808 | A | 2/1994 | Kovac et al. |
| 5,282,827 | A | 2/1994 | Kensey et al. |
| 5,282,832 | A | 2/1994 | Toso et al. |
| 5,289,963 | A | 3/1994 | McGarry et al. |
| 5,290,243 | A | 3/1994 | Chodorow et al. |
| 5,290,310 | A | 3/1994 | Makower et al. |
| 5,292,309 | A | 3/1994 | Van Tassel et al. |
| 5,292,332 | A | 3/1994 | Lee |
| 5,304,184 | A | 4/1994 | Hathaway et al. |
| 5,304,204 | A | 4/1994 | Bregen |
| 5,306,254 | A | 4/1994 | Nash et al. |
| 5,306,280 | A | 4/1994 | Bregen et al. |
| 5,318,542 | A | 6/1994 | Hirsch et al. |
| 5,320,639 | A | 6/1994 | Rudnick |
| 5,330,442 | A | 7/1994 | Green et al. |
| 5,330,445 | A | 7/1994 | Haaga |
| 5,334,216 | A | 8/1994 | Vidal et al. |
| 5,334,217 | A | 8/1994 | Das |
| 5,335,680 | A | 8/1994 | Moore |
| 5,340,360 | A | 8/1994 | Stefanchik |
| 5,350,399 | A | 9/1994 | Erlebacher et al. |
| 5,352,229 | A | 10/1994 | Goble et al. |
| 5,364,406 | A | 11/1994 | Sewell, Jr. |
| 5,364,408 | A | 11/1994 | Gordon |
| 5,366,458 | A | 11/1994 | Korthoff et al. |
| 5,366,479 | A | 11/1994 | McGarry et al. |
| 5,376,101 | A | 12/1994 | Green et al. |
| 5,383,896 | A | 1/1995 | Gershony et al. |
| 5,383,905 | A | 1/1995 | Golds et al. |
| RE34,866 | E | 2/1995 | Kensey et al. |
| 5,391,173 | A | 2/1995 | Wilk |
| 5,392,978 | A | 2/1995 | Valez et al. |
| 5,395,030 | A | 3/1995 | Kuramoto et al. |
| 5,409,499 | A | 4/1995 | Yi |
| 5,411,520 | A | 5/1995 | Nash et al. |
| 5,413,571 | A | 5/1995 | Katsaros et al. |
| 5,413,584 | A | 5/1995 | Schulze |
| 5,416,584 | A | 5/1995 | Kay |
| 5,417,699 | A | 5/1995 | Klein et al. |
| 5,419,777 | A | 5/1995 | Hofling |
| 5,423,857 | A | 6/1995 | Rosenman et al. |
| 5,425,489 | A | 6/1995 | Shichman et al. |
| 5,425,740 | A | 6/1995 | Hutchinson, Jr. |
| 5,431,639 | A | 7/1995 | Shaw |
| 5,431,667 | A | 7/1995 | Thompson et al. |
| 5,433,721 | A | 7/1995 | Hooven et al. |
| 5,437,631 | A | 8/1995 | Janzen |
| 5,439,479 | A | 8/1995 | Shichman et al. |
| 5,443,481 | A | 8/1995 | Lee |
| 5,449,359 | A | 9/1995 | Groiso |
| 5,456,400 | A | 10/1995 | Shichman et al. |
| 5,462,558 | A | 10/1995 | Kolesa et al. |
| 5,462,561 | A | 10/1995 | Voda |
| 5,466,241 | A | 11/1995 | Leroy et al. |
| 5,470,010 | A | 11/1995 | Rothfuss et al. |
| 5,474,557 | A | 12/1995 | Mai |
| 5,474,572 | A | 12/1995 | Hayhurst |
| 5,478,352 | A | 12/1995 | Fowler |
| 5,478,353 | A | 12/1995 | Yoon |
| 5,478,354 | A | 12/1995 | Tovey et al. |
| 5,486,195 | A | 1/1996 | Myers et al. |
| 5,497,933 | A | 3/1996 | DeFonzo et al. |
| 5,501,698 | A | 3/1996 | Roth et al. |
| 5,507,744 | A | 4/1996 | Tay et al. |
| 5,507,755 | A | 4/1996 | Gresl et al. |
| 5,514,159 | A | 5/1996 | Matula et al. |
| 5,521,184 | A | 5/1996 | Zimmerman |
| 5,522,840 | A | 6/1996 | Krajicek |
| 5,527,322 | A | 6/1996 | Klein et al. |
| 5,536,251 | A | 7/1996 | Evard et al. |
| 5,540,712 | A | 7/1996 | Kleshinski et al. |
| 5,540,716 | A | 7/1996 | Hlavacek |
| 5,543,520 | A | 8/1996 | Zimmerman |
| 5,544,802 | A | 8/1996 | Crainich |
| 5,547,474 | A | 8/1996 | Kloeckl et al. |
| 5,560,532 | A | 10/1996 | DeFonzo et al. |
| 5,571,120 | A | 11/1996 | Yoon |
| 5,575,771 | A | 11/1996 | Walinsky |
| 5,584,879 | A | 12/1996 | Reimold et al. |
| 5,591,205 | A | 1/1997 | Fowler |
| 5,593,412 | A | 1/1997 | Martinez |
| 5,593,422 | A | 1/1997 | Van de Moer et al. |
| 5,593,425 | A | 1/1997 | Bonutti et al. |
| 5,601,602 | A | 2/1997 | Fowler |
| 5,609,597 | A | 3/1997 | Lehrer |
| 5,611,986 | A | 3/1997 | Datta et al. |
| 5,613,974 | A | 3/1997 | Andreas et al. |
| 5,618,291 | A | 4/1997 | Thompson et al. |
| 5,618,306 | A | 4/1997 | Roth et al. |
| 5,620,452 | A | 4/1997 | Yoon |
| 5,620,461 | A | 4/1997 | Muijs Van De Moer et al. |
| 5,630,824 | A | 5/1997 | Hart |
| 5,643,318 | A | 7/1997 | Tsukernik et al. |
| 5,645,553 | A | 7/1997 | Kolesa et al. |
| 5,645,565 | A | 7/1997 | Rudd et al. |
| 5,645,566 | A | 7/1997 | Brenneman et al. |
| 5,645,567 | A | 7/1997 | Crainich |
| 5,649,959 | A | 7/1997 | Hannam et al. |
| D383,539 | S | 9/1997 | Croley |
| 5,669,917 | A | 9/1997 | Sauer et al. |
| 5,674,231 | A | 10/1997 | Green et al. |
| 5,676,689 | A | 10/1997 | Kensey et al. |
| 5,676,974 | A | 10/1997 | Valdes et al. |
| 5,681,351 | A | 10/1997 | Jamiolkowski et al. |
| 5,683,405 | A | 11/1997 | Yacoubian et al. |
| 5,690,674 | A | 11/1997 | Diaz |
| 5,695,504 | A | 12/1997 | Gifford, III et al. |
| 5,695,505 | A | 12/1997 | Yoon |
| 5,695,524 | A | 12/1997 | Kelley et al. |
| 5,700,273 | A | 12/1997 | Buelna et al. |
| 5,709,708 | A | 1/1998 | Thal |
| 5,716,375 | A | 2/1998 | Fowler |
| 5,720,755 | A | 2/1998 | Dakov |
| 5,720,765 | A | 2/1998 | Thal |

| | | | | | | |
|---|---|---|---|---|---|---|
| 5,725,554 A | 3/1998 | Simon et al. | 5,957,936 A | 9/1999 | Yoon et al. | |
| 5,725,556 A | 3/1998 | Moser et al. | 5,957,938 A | 9/1999 | Zhu et al. | |
| 5,728,109 A | 3/1998 | Schulze et al. | 5,964,782 A | 10/1999 | Lafontaine et al. | |
| 5,728,110 A | 3/1998 | Vidal et al. | 5,976,159 A | 11/1999 | Bolduc et al. | |
| 5,728,114 A | 3/1998 | Evans et al. | 5,976,161 A | 11/1999 | Kirsch et al. | |
| 5,728,122 A | 3/1998 | Leschinsky et al. | 5,984,934 A | 11/1999 | Ashby et al. | |
| 5,728,132 A | 3/1998 | Van Tassel et al. | 5,984,949 A | 11/1999 | Levin | |
| 5,732,872 A | 3/1998 | Bolduc et al. | 5,993,468 A | 11/1999 | Rygaard | |
| 5,735,873 A | 4/1998 | MacLean | 5,993,476 A | 11/1999 | Groiso | |
| 5,735,875 A | 4/1998 | Bonutti et al. | 6,001,110 A | 12/1999 | Adams | |
| 5,735,877 A | 4/1998 | Pagedas | 6,004,341 A | 12/1999 | Zhu et al. | |
| 5,749,898 A | 5/1998 | Schulze et al. | 6,007,563 A | 12/1999 | Nash et al. | |
| 5,752,966 A | 5/1998 | Chang | 6,013,084 A | 1/2000 | Ken et al. | |
| 5,755,726 A | 5/1998 | Pratt et al. | 6,022,372 A | 2/2000 | Kontos | |
| 5,755,778 A | 5/1998 | Kleshinski | 6,024,750 A | 2/2000 | Mastri et al. | |
| 5,766,217 A | 6/1998 | Christy | 6,024,758 A | 2/2000 | Thal | |
| 5,766,246 A | 6/1998 | Mulhauser et al. | 6,030,364 A | 2/2000 | Durgin et al. | |
| 5,769,862 A | 6/1998 | Kammerer et al. | 6,030,413 A | 2/2000 | Lazarus | |
| 5,769,870 A | 6/1998 | Salahieh et al. | 6,033,427 A | 3/2000 | Lee | |
| 5,776,150 A | 7/1998 | Nolan et al. | 6,036,703 A | 3/2000 | Evans et al. | |
| 5,779,707 A | 7/1998 | Bertholet et al. | 6,036,720 A | 3/2000 | Abrams et al. | |
| 5,782,844 A | 7/1998 | Yoon et al. | 6,045,570 A | 4/2000 | Epstein et al. | |
| 5,782,860 A | 7/1998 | Epstein et al. | 6,048,358 A | 4/2000 | Barak | |
| 5,782,861 A | 7/1998 | Cragg et al. | 6,056,768 A | 5/2000 | Cates et al. | |
| 5,782,864 A | 7/1998 | Lizardi | 6,056,769 A | 5/2000 | Epstein et al. | |
| 5,795,958 A | 8/1998 | Rao et al. | 6,056,770 A | 5/2000 | Epstein et al. | |
| 5,797,928 A | 8/1998 | Kogasaka | 6,059,800 A | 5/2000 | Hart et al. | |
| 5,797,931 A | 8/1998 | Bito et al. | 6,063,085 A | 5/2000 | Tay et al. | |
| 5,797,933 A | 8/1998 | Snow et al. | 6,063,114 A | 5/2000 | Nash et al. | |
| 5,797,958 A | 8/1998 | Yoon | 6,066,160 A | 5/2000 | Colvin et al. | |
| 5,810,776 A | 9/1998 | Bacich et al. | 6,071,300 A | 6/2000 | Brenneman et al. | |
| 5,810,846 A | 9/1998 | Virnich et al. | 6,074,409 A | 6/2000 | Goldfarb | |
| 5,810,851 A | 9/1998 | Yoon | 6,077,281 A | 6/2000 | Das | |
| 5,810,877 A | 9/1998 | Roth et al. | 6,077,291 A | 6/2000 | Das | |
| 5,814,069 A | 9/1998 | Schulze et al. | 6,080,182 A | 6/2000 | Shaw et al. | |
| 5,817,113 A | 10/1998 | Gifford, III et al. | 6,080,183 A | 6/2000 | Tsugita et al. | |
| 5,820,631 A | 10/1998 | Nobles | 6,086,608 A | 7/2000 | Ek et al. | |
| 5,827,298 A | 10/1998 | Hart et al. | 6,090,130 A | 7/2000 | Nash et al. | |
| 5,830,125 A | 11/1998 | Scribner et al. | 6,092,561 A | 7/2000 | Schmid | |
| 5,833,698 A | 11/1998 | Hinchliffe et al. | 6,099,553 A | 8/2000 | Hart et al. | |
| 5,843,167 A | 12/1998 | Dwyer et al. | 6,102,271 A | 8/2000 | Longo et al. | |
| 5,846,254 A | 12/1998 | Schulze et al. | 6,106,545 A | 8/2000 | Egan | |
| 5,853,421 A | 12/1998 | Leschinsky et al. | 6,110,184 A | 8/2000 | Weadock | |
| 5,853,422 A | 12/1998 | Huebsch et al. | 6,113,612 A | 9/2000 | Swanson et al. | |
| 5,855,312 A | 1/1999 | Toledano | 6,117,125 A | 9/2000 | Rothbarth et al. | |
| 5,858,082 A | 1/1999 | Cruz et al. | 6,117,148 A | 9/2000 | Ravo | |
| 5,860,991 A | 1/1999 | Klein et al. | 6,120,524 A * | 9/2000 | Taheri | 606/213 |
| 5,861,005 A | 1/1999 | Kontos | 6,126,675 A | 10/2000 | Shchervinsky et al. | |
| 5,868,755 A | 2/1999 | Kanner et al. | 6,126,677 A | 10/2000 | Ganaja et al. | |
| 5,868,763 A | 2/1999 | Spence et al. | 6,143,017 A | 11/2000 | Thal | |
| 5,871,474 A | 2/1999 | Hermann et al. | 6,149,660 A | 11/2000 | Laufer et al. | |
| 5,871,490 A | 2/1999 | Schulze et al. | 6,149,667 A | 11/2000 | Hovland et al. | |
| 5,871,501 A | 2/1999 | Leschinsky et al. | 6,152,144 A | 11/2000 | Lesh et al. | |
| 5,871,525 A | 2/1999 | Edwards et al. | 6,152,934 A | 11/2000 | Harper et al. | |
| 5,873,876 A | 2/1999 | Christy | 6,152,936 A | 11/2000 | Christy et al. | |
| 5,879,366 A | 3/1999 | Shaw et al. | 6,152,937 A | 11/2000 | Peterson et al. | |
| 5,893,592 A | 4/1999 | Schulze et al. | 6,159,234 A | 12/2000 | Bonutti et al. | |
| 5,897,487 A | 4/1999 | Ouchi | 6,165,204 A | 12/2000 | Levinson et al. | |
| 5,902,310 A | 5/1999 | Foerster et al. | 6,174,324 B1 | 1/2001 | Egan et al. | |
| 5,904,697 A | 5/1999 | Gifford, III et al. | 6,193,734 B1 | 2/2001 | Bolduc et al. | |
| 5,906,631 A | 5/1999 | Imran | 6,197,042 B1 | 3/2001 | Ginn et al. | |
| 5,907,893 A | 6/1999 | Zadno-Azizi et al. | 6,200,329 B1 | 3/2001 | Fung et al. | |
| 5,910,155 A | 6/1999 | Ratcliff et al. | 6,203,565 B1 | 3/2001 | Bonutti et al. | |
| 5,919,207 A | 7/1999 | Taheri | 6,206,913 B1 | 3/2001 | Yencho et al. | |
| 5,919,208 A | 7/1999 | Valenti | 6,220,248 B1 | 4/2001 | Voegele et al. | |
| 5,922,009 A | 7/1999 | Epstein et al. | 6,221,102 B1 | 4/2001 | Baker et al. | |
| 5,935,147 A | 8/1999 | Kensey et al. | 6,231,592 B1 | 5/2001 | Bonutti et al. | |
| 5,938,667 A | 8/1999 | Peyser et al. | 6,248,124 B1 | 6/2001 | Pedros et al. | |
| 5,941,890 A | 8/1999 | Voegele et al. | 6,254,615 B1 | 7/2001 | Bolduc et al. | |
| 5,947,999 A | 9/1999 | Groiso | 6,254,617 B1 | 7/2001 | Spence et al. | |
| 5,951,518 A | 9/1999 | Licata et al. | 6,254,642 B1 | 7/2001 | Taylor | |
| 5,951,576 A | 9/1999 | Wakabayashi | 6,277,140 B2 | 8/2001 | Ginn et al. | |
| 5,951,589 A | 9/1999 | Epstein et al. | 6,280,460 B1 | 8/2001 | Bolduc et al. | |

| | | | | | | |
|---|---|---|---|---|---|---|
| 6,287,322 B1 | 9/2001 | Zhu et al. | | 6,890,343 B2 | 5/2005 | Ginn et al. |
| 6,296,657 B1 | 10/2001 | Brucker | | 6,896,687 B2 | 5/2005 | Dakov |
| 6,305,891 B1 | 10/2001 | Burlingame | | 6,896,692 B2 | 5/2005 | Ginn et al. |
| 6,319,258 B1 | 11/2001 | McAllen, III et al. | | 6,926,723 B1 | 8/2005 | Mulhauser et al. |
| 6,322,580 B1 | 11/2001 | Kanner | | 6,926,731 B2 | 8/2005 | Coleman et al. |
| 6,334,865 B1 | 1/2002 | Redmond et al. | | 6,942,674 B2 | 9/2005 | Belef et al. |
| 6,348,064 B1 | 2/2002 | Kanner | | 6,942,691 B1 | 9/2005 | Chuter |
| 6,358,258 B1 | 3/2002 | Arcia et al. | | 6,969,397 B2 | 11/2005 | Ginn |
| D457,958 S | 5/2002 | Dycus | | 6,989,003 B2 | 1/2006 | Wing et al. |
| 6,383,208 B1 | 5/2002 | Sancoff et al. | | 6,989,016 B2 | 1/2006 | Tallarida et al. |
| 6,391,048 B1 | 5/2002 | Ginn et al. | | 7,001,398 B2 | 2/2006 | Carley et al. |
| 6,395,015 B1 | 5/2002 | Borst et al. | | 7,008,435 B2 | 3/2006 | Cummins |
| 6,398,752 B1 | 6/2002 | Sweezer et al. | | 7,033,379 B2 | 4/2006 | Peterson |
| 6,402,765 B1 | 6/2002 | Monassevitch et al. | | 7,060,084 B1 | 6/2006 | Loshakove et al. |
| 6,409,739 B1 | 6/2002 | Nobles et al. | | 7,063,711 B1 | 6/2006 | Loshakove et al. |
| 6,419,669 B1 | 7/2002 | Frazier et al. | | 7,083,635 B2 | 8/2006 | Ginn |
| 6,423,054 B1 | 7/2002 | Ouchi | | 7,108,709 B2 | 9/2006 | Cummins |
| 6,428,472 B1 | 8/2002 | Haas | | 7,108,710 B2 | 9/2006 | Anderson |
| 6,428,548 B1 | 8/2002 | Durgin et al. | | 7,111,768 B2 | 9/2006 | Cummins et al. |
| 6,443,158 B1 | 9/2002 | Lafontaine et al. | | 7,112,225 B2 | 9/2006 | Ginn |
| 6,443,963 B1 | 9/2002 | Baldwin et al. | | 7,144,411 B2 | 12/2006 | Ginn et al. |
| 6,447,540 B1 | 9/2002 | Fontaine et al. | | 7,163,551 B2 | 1/2007 | Anthony et al. |
| 6,450,391 B1 | 9/2002 | Kayan et al. | | 7,169,158 B2 | 1/2007 | Sniffin et al. |
| 6,458,130 B1 | 10/2002 | Frazier et al. | | 7,169,164 B2 | 1/2007 | Borillo et al. |
| 6,461,364 B1 | 10/2002 | Ginn et al. | | 7,211,101 B2 | 5/2007 | Carley et al. |
| 6,482,224 B1 | 11/2002 | Michler et al. | | 7,316,704 B2 | 1/2008 | Bagaoisan et al. |
| 6,488,692 B1 | 12/2002 | Spence et al. | | 7,326,230 B2 | 2/2008 | Ravikumar |
| 6,500,115 B2 | 12/2002 | Krattiger et al. | | 7,331,979 B2 | 2/2008 | Khosravi et al. |
| 6,506,210 B1 | 1/2003 | Kanner | | 7,335,220 B2 | 2/2008 | Khosravi et al. |
| 6,517,569 B2 | 2/2003 | Mikus et al. | | D566,272 S | 4/2008 | Walberg et al. |
| 6,533,762 B2 | 3/2003 | Kanner et al. | | 7,361,183 B2 | 4/2008 | Ginn |
| 6,533,812 B2 | 3/2003 | Swanson et al. | | 7,361,185 B2 | 4/2008 | O'Malley et al. |
| 6,537,288 B2 | 3/2003 | Vargas et al. | | 7,393,363 B2 | 7/2008 | Ginn |
| 6,547,806 B1 | 4/2003 | Ding | | 7,396,359 B1 | 7/2008 | Derowe et al. |
| 6,569,173 B1 | 5/2003 | Blatter et al. | | 7,597,706 B2 | 10/2009 | Kanner et al. |
| 6,569,185 B2 | 5/2003 | Ungs | | 2001/0007077 A1 | 7/2001 | Ginn et al. |
| 6,572,629 B2 | 6/2003 | Kalloo et al. | | 2001/0031972 A1 | 10/2001 | Robertson et al. |
| 6,582,452 B2 | 6/2003 | Coleman et al. | | 2001/0046518 A1 | 11/2001 | Sawhney |
| 6,582,482 B2 | 6/2003 | Gillman et al. | | 2001/0047180 A1 | 11/2001 | Grudem et al. |
| 6,599,303 B1 | 7/2003 | Peterson et al. | | 2002/0026208 A1 | 2/2002 | Belef |
| 6,602,263 B1 | 8/2003 | Swanson et al. | | 2002/0026215 A1 | 2/2002 | Redmond et al. |
| 6,610,072 B1 | 8/2003 | Christy et al. | | 2002/0038127 A1 | 3/2002 | Blatter et al. |
| 6,613,059 B2 | 9/2003 | Schaller et al. | | 2002/0042622 A1 | 4/2002 | Vargas et al. |
| 6,616,686 B2 | 9/2003 | Coleman et al. | | 2002/0049427 A1 | 4/2002 | Wiener et al. |
| 6,623,509 B2 | 9/2003 | Ginn | | 2002/0049472 A1 | 4/2002 | Coleman |
| 6,623,510 B2 | 9/2003 | Carley et al. | | 2002/0058960 A1 | 5/2002 | Hudson et al. |
| 6,626,918 B1 | 9/2003 | Ginn et al. | | 2002/0072768 A1 | 6/2002 | Ginn |
| 6,632,238 B2 | 10/2003 | Ginn et al. | | 2002/0077657 A1 | 6/2002 | Ginn et al. |
| 6,634,537 B2 | 10/2003 | Chen | | 2002/0082641 A1 | 6/2002 | Ginn et al. |
| 6,645,205 B2 | 11/2003 | Ginn | | 2002/0099389 A1 | 7/2002 | Michler et al. |
| 6,652,538 B2 | 11/2003 | Kayan et al. | | 2002/0106409 A1 | 8/2002 | Sawhney et al. |
| 6,652,556 B1 | 11/2003 | VanTassel et al. | | 2002/0107542 A1 | 8/2002 | Kanner et al. |
| 6,663,655 B2 | 12/2003 | Ginn et al. | | 2002/0133193 A1 | 9/2002 | Ginn et al. |
| 6,669,714 B2 | 12/2003 | Coleman et al. | | 2002/0151921 A1 | 10/2002 | Kanner et al. |
| 6,676,671 B2 | 1/2004 | Robertson et al. | | 2002/0188318 A1 | 12/2002 | Carley et al. |
| 6,676,685 B2 | 1/2004 | Pedros et al. | | 2002/0193808 A1 | 12/2002 | Belef et al. |
| 6,679,904 B2 | 1/2004 | Gleeson et al. | | 2003/0004543 A1 | 1/2003 | Gleeson et al. |
| 6,689,147 B1 | 2/2004 | Koster, Jr. | | 2003/0009180 A1 | 1/2003 | Hinchliffe et al. |
| 6,695,867 B2 | 2/2004 | Ginn et al. | | 2003/0009196 A1 | 1/2003 | Peterson |
| 6,699,256 B1 | 3/2004 | Logan et al. | | 2003/0032981 A1 | 2/2003 | Kanner et al. |
| 6,702,826 B2 | 3/2004 | Liddicoat et al. | | 2003/0065358 A1 | 4/2003 | Frecker et al. |
| 6,712,836 B1 | 3/2004 | Berg et al. | | 2003/0078598 A1 | 4/2003 | Ginn et al. |
| 6,719,777 B2 | 4/2004 | Ginn et al. | | 2003/0083679 A1 | 5/2003 | Grudem et al. |
| 6,726,704 B1 | 4/2004 | Loshakove et al. | | 2003/0093096 A1 | 5/2003 | McGuckin et al. |
| 6,743,195 B2 | 6/2004 | Zucker | | 2003/0097140 A1 | 5/2003 | Kanner |
| 6,743,259 B2 | 6/2004 | Ginn | | 2003/0109890 A1 | 6/2003 | Kanner et al. |
| 6,749,621 B2 | 6/2004 | Pantages et al. | | 2003/0125766 A1 | 7/2003 | Ding |
| 6,749,622 B2 | 6/2004 | McGuckin et al. | | 2003/0158577 A1 | 8/2003 | Pantages et al. |
| 6,755,842 B2 | 6/2004 | Kanner et al. | | 2003/0158578 A1 | 8/2003 | Pantages et al. |
| 6,767,356 B2 | 7/2004 | Kanner et al. | | 2003/0195504 A1 | 10/2003 | Tallarida et al. |
| 6,780,197 B2 | 8/2004 | Roe et al. | | 2003/0195561 A1 | 10/2003 | Carley et al. |
| 6,837,906 B2 | 1/2005 | Ginn | | 2004/0009205 A1 | 1/2004 | Sawhney |
| 6,846,319 B2 | 1/2005 | Ginn et al. | | 2004/0009289 A1 | 1/2004 | Carley et al. |

| | | |
|---|---|---|
| 2004/0010285 A1 | 1/2004 | Carley et al. |
| 2004/0039414 A1 | 2/2004 | Carley et al. |
| 2004/0073236 A1 | 4/2004 | Carley et al. |
| 2004/0073255 A1 | 4/2004 | Ginn et al. |
| 2004/0082906 A1 | 4/2004 | Tallarida et al. |
| 2004/0087985 A1 | 5/2004 | Loshakove et al. |
| 2004/0092968 A1 | 5/2004 | Caro et al. |
| 2004/0093027 A1 | 5/2004 | Fabisiak et al. |
| 2004/0127940 A1 | 7/2004 | Ginn et al. |
| 2004/0143290 A1 | 7/2004 | Brightbill |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0165357 A1 | 7/2005 | McGuckin et al. |
| 2005/0177189 A1 | 8/2005 | Ginn et al. |
| 2005/0216057 A1 | 9/2005 | Coleman et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0034930 A1 | 2/2006 | Khosravi et al. |
| 2006/0047313 A1 | 3/2006 | Khanna et al. |
| 2006/0100664 A1 | 5/2006 | Pai et al. |
| 2006/0135989 A1 | 6/2006 | Carley et al. |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190037 A1 | 8/2006 | Carley et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0253037 A1 | 11/2006 | Ginn et al. |
| 2006/0253072 A1 | 11/2006 | Pai et al. |
| 2006/0265012 A1 | 11/2006 | Anderson |
| 2006/0287674 A1 | 12/2006 | Ginn et al. |
| 2007/0010853 A1 | 1/2007 | Ginn et al. |
| 2007/0010854 A1 | 1/2007 | Cummins et al. |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0123817 A1 | 5/2007 | Khosravi et al. |
| 2007/0203506 A1 | 8/2007 | Sibbitt, Jr. et al. |
| 2007/0250080 A1 | 10/2007 | Jones et al. |
| 2007/0270904 A1 | 11/2007 | Ginn |
| 2007/0276416 A1 | 11/2007 | Ginn et al. |
| 2007/0282352 A1 | 12/2007 | Carley et al. |
| 2008/0004636 A1 | 1/2008 | Walberg |
| 2008/0009794 A1 | 1/2008 | Bagaoisan et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0269802 A1 | 5/2008 | Coleman et al. |
| 2008/0210737 A1 | 9/2008 | Ginn et al. |
| 2008/0221616 A1 | 9/2008 | Ginn et al. |
| 2008/0269801 A1 | 10/2008 | Coleman et al. |
| 2008/0272173 A1 | 11/2008 | Coleman et al. |
| 2008/0312666 A1 | 12/2008 | Ellingwood et al. |
| 2008/0312686 A1 | 12/2008 | Ellingwood |
| 2008/0319475 A1 | 12/2008 | Clark |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0254119 A1 | 10/2009 | Sibbitt, Jr. et al. |
| 2010/0130965 A1 | 5/2010 | Sibbitt, Jr. |

FOREIGN PATENT DOCUMENTS

| | | |
|---|---|---|
| DE | 197 11 288 | 1/1998 |
| DE | 297 23 736 U 1 | 4/1999 |
| DE | 19859952 | 2/2000 |
| EP | 0 386 361 | 9/1990 |
| EP | 0 534 696 | 3/1993 |
| EP | 0 756 851 | 2/1997 |
| EP | 0 774 237 | 5/1997 |
| EP | 0 858 776 | 8/1998 |
| EP | 0 941 697 | 9/1999 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| IE | S 2000/0722 | 10/2001 |
| IE | S 2000/0724 | 10/2001 |
| IE | S 2001/0547 | 7/2002 |
| IE | S 2001/0815 | 7/2002 |
| IE | S 2001/0748 | 8/2002 |
| IE | S 2001/0749 | 8/2002 |
| IE | S 2002/0664 | 2/2003 |
| IE | S 2002/0665 | 2/2003 |
| IE | S 2002/0451 | 7/2003 |
| IE | S 2003/0424 | 12/2003 |
| IE | S 2003/0490 | 1/2004 |
| IE | S 2004/0368 | 11/2005 |
| IE | S 2005/0342 | 11/2005 |
| JP | 58-181006 | 12/1983 |
| JP | 1 2 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 197801 | 6/1967 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |

| | | |
|---|---|---|
| WO | WO 98/58591 | 12/1998 |
| WO | WO 99/21491 | 5/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO-00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19924 | 3/2002 |
| WO | WO 02/02/28286 | 4/2002 |
| WO | WO 02/38055 | 5/2002 |
| WO | WO 02/45593 | 6/2002 |
| WO | WO 02/45594 | 6/2002 |
| WO | WO 02/62234 | 8/2002 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/94748 | 11/2003 |
| WO | WO 2004/004578 | 1/2004 |
| WO | WO 2004/060169 | 7/2004 |
| WO | WO 2004/069054 | 8/2004 |
| WO | WO 2005/000126 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2008/031102 | 3/2008 |
| WO | WO 2009/079091 | 6/2009 |
| WO | WO 2010/031050 | 3/2010 |
| ZA | 20010527 | 1/2001 |
| ZA | 200100528 | 1/2001 |

OTHER PUBLICATIONS

U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
Stretch Comb by Scunci, retrieved via internet at www.scunci.com/productdetail by examiner on Oct. 9, 2007, publication date unavailable.
"Hand tool for forming telephone connections—comprises pliers with reciprocably driven ram crimping clip around conductors against anvil", Derwent-ACC-No. 1978-B8090A.
U.S. Appl. No. 09/732,178, filed Aug. 1, 2002, Office Action.
U.S. Appl. No. 09/732,178, filed Dec. 24, 2002, Office Action.
U.S. Appl. No. 09/732,178, filed Jun. 10, 2003, Advisory Action.
U.S. Appl. No. 09/732,178, filed Jul. 3, 2003, Office Action.
U.S. Appl. No. 09/732,178, filed Nov. 17, 2003, Notice of Allowance.
U.S. Appl. No. 10/081,725, filed Apr. 13, 2004, Office Action.
U.S. Appl. No. 10/356,214, filed Mar. 6, 2008, Office Action.
U.S. Appl. No. 10/541,083, filed May 5, 2008, Office Action.
U.S. Appl. No. 10/435,104, filed May 23, 2007, Issue Notification.
U.S. Appl. No. 10/435,104, filed Oct. 26, 2007, Notice of Allowance.
U.S. Appl. No. 10/435,104, filed Apr. 4, 2008, Notice of Allowance.
U.S. Appl. No. 10/787,073, filed Feb. 22, 2008, Office Action.
U.S. Appl. No. 10/616,832, filed Jan. 22, 2008, Office Action.
U.S. Appl. No. 10/667,144, filed Nov. 19, 2007, Office Action.
U.S. Appl. No. 10/667,144, filed Dec. 5, 2007, Office Action.
U.S. Appl. No. 10/667,144, filed May 12, 2008, Office Action.
U.S. Appl. No. 11/113,549, filed Nov. 9, 2007, Office Action.
U.S. Appl. No. 11/113,549, filed Apr. 16, 2008, Office Action.
U.S. Appl. No. 10/682,459, filed Apr. 2, 2008, Office Action.
U.S. Appl. No. 10/786,444, filed Apr. 24, 2008, Office Action.
U.S. Appl. No. 10/638,115, filed Feb. 7, 2008, Office Action.
U.S. Appl. No. 10/264,306, filed May 26, 2005, Office Action.
U.S. Appl. No. 10/264,306, filed Feb. 4, 2008, Notice of Allowance.
U.S. Appl. No. 11/406,203, filed Jan. 29, 2008, Notice of Allowance.
U.S. Appl. No. 11/406,203, filed May 23, 2008, Notice of Allowance.
U.S. Appl. No. 11/411,925, filed Feb. 5, 2008, Office Action.
U.S. Appl. No. 10/147,774, filed Feb. 6, 2008, Notice of Allowance.
U.S. Appl. No. 10/006,400, filed Apr. 2, 2008, Office Action.
U.S. Appl. No. 11/152,562, filed May 13, 2008, Office Action.
U.S. Appl. No. 10/908,721, filed Jan. 25, 2008, Office Action.
U.S. Appl. No. 11/344,891, filed Apr. 29, 2008, Office Action.
U.S. Appl. No. 10/616,832, Mail Date Sep. 17, 2008, Office Action.
Scott Hensley, Closing Wounds. New Devices seal arterial punctures in double time, Modern healthcare (United States), Mar. 23, 2008, p. 48.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25 - No. 7.
OM Elashry et al, Comparative clinical study of port-closure techniques following laparoscopic surgery, Department of Surgery, Mallickrodt Institute of Radiography, J Am Coll Surg., Oct 1996, pp. 335-344, vol. 183 - No. 4.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25. - No. 2, Supplement 1.
Tomoaki Hinohara, Percutaneous vascular surgery (Prostar® Plus and Techstar® for femoral artery site closure), Interventional Cardiology Newsletter, May-Jul. 1997, pp. 19-28, vol. 5 - No. 3-4.
Sigmund Silber et al, A novel vascular device for closure of percutaneous arterial access sites, The American Jornal of Cardiology, Apr. 1999, pp. 1248-1252, vol. 83 - No. 8.
Wei Qu et al, An absorbable pinned-ring device for microvascular anastomosis of vein grafts: Experimental studies, Microsurgery 1999, Mar. 1999, pp. 128-134, vol. 19 - No. 3, Department of Orthopaedic Surgery, Hiroshima University School of Medicine, Hiroshima, Japan.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
P M N Werker, et al, Review of facilitated approaches to vascular anastomosis surgery towards minimally invasive coronary artery bypass grafting, Conference: Utrecht MICABG Workshop 2, The Annals of thoracic surgery, Apr. 1996, pp. 122-127, vol. 63 - No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

H DE Swart et al, A new hemostatic puncture closure device for the immediate sealing of arterial puncture sites, American journal of cardiology, Aug. 1993, pp. 445-449, vol. 72 - No. 5, Department of Cardiology, Academic Hospital Maastricht, The Netherlands.

DL Wessel et al, Outpatient closure of the patent ductus arteriosus, Circulation, May 1988, pp. 1068-1071, vol. 77 - No. 5, Department of Anesthesia, Children's Hospital, Boston, MA.

SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19 - No. 6, Gen Hosp North, Dept Dianost & Intervent Radiol, Nurnberg, Germany (Reprint).

Swee Lian Tan, MD, PHD, FACS, Explanation of Infected Hemostatic Puncture Closure Devices - A Case Report, Vascular and Endovascular Surgery, 1999, pp. 507-510, vol. 33 - No. 5, Parkland Medical Center, Derry, New Hampshire.

Ut Aker et al, Immediate arterial hemostasis after cardiac catheterization: initial experience with a new puncture closure device, Cathet Cardiovasc Diagn, Mar. 1994, pp. 228-232, vol. 33 - No. 3, Missouri Baptist Medical Center, St. Louis.

Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.

E Pikoulis et al, Arterial reconstruction with vascular clips is safe and quicker than sutured repair, Cardiovascular Surgery, Dec. 1998, pp. 573-578(6), vol. 6 - No. 6, Department of Surgery, Uniformed Services University of the Health Sciences, Bethesda, MD.

SY Nakada et al, Comparison of newer laparoscopic port closure techniques in the porcine model, J Endourol, Oct. 1995, pp. 397-401, vol. 9 - No. 5, Department of Surgery/Urology, University of Wisconsin Medical School, Madison.

MD Hellinger et al, Effective peritoneal and fascial closure of abdominal trocar sites utilizing the Endo-Judge, J Laparoendosc Surg., Oct. 1996, pp. 329-332, vol. 6 - No. 5, Orlando Regional Medical Center, FL.

K Narayanan et al, Simultaneous primary closure of four fasciotomy wounds in a single setting using the Sure-Closure device, Injury, Jul. 1996, pp. 449-451, vol. 27 - No. 6, Department of Surgery, Mercy Hospital of Pittsburgh, PA.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

Peter Rhee MD et al, Use of Titanium Vascular Staples in Trauma, Journal of Trauma-Injury Infection & Critical Care, Dec. 1998, pp. 1097-1099, vol. 45 - No. 6, Institution from the Department of Surgery, Washington Hospital Center, Washington DC, and Uniformed Services University of the Health Sciences, Bethesda, Maryland.

J. Findlay et al, Carotid Arteriotomy Closure Using a Vascular Clip System, Neurosurgery, Mar. 1998, pp. 550-554, vol. 42 - No. 3, Division of Neurosurgery, University of Alberta, Edmonton, Canada.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42 - No. 3, Institution Department of Plastic and Reconstructive Surgery, Albert Einstein College of Medicine and Montefiore Medical Center, Bronx, NY.

Jeremy L Gilbert PHD, Wound Closure Biomaterials And Devices, Shock., Mar. 1999, p. 226, vol. 11- No. 3, Institution Northwestern University.

Deepak Mital et al, Renal Transplantation Without Sutures Using The Vascular Clipping System For Renal Artery And Vein Anastomosis—A New Technique, Transplantation Issue, Oct. 1996, pp. 1171-1173, vol. 62 - No. 8, Section of Transplantation Surgery, Department of General Surgery, Rush-Presbyterian/St. Luke's Medical Center, Chigago, IL.

Michael Gianturco, A Play on Catheterization, Forbes, Dec. 1996, p. 146, vol. 158 - No. 15.

Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5 - No. 2, Division of Obstetrics and Gynecology, University of Chicago, Chigago, IL.

G Gershony et al, Novel vascular sealing device for closure of percutaneous vascular access sites, Cathet. Cardiovasc. Diagn., Jan. 1998, pp. 82-88, vol. 45.

U.S. Appl. No. 10/435,104, Mail Date Sep. 26, 2008, Notice of Allowance.
U.S. Appl. No. 10/541,083, Mail Date Sep. 19, 2008, Notice of Allowance.
U.S. Appl. No. 11/406,203, Mail Date Sep. 22, 2008, Notice of Allowance.
U.S. Appl. No. 10/147,774, Mail Date Jun. 30, 2008, Office Action.
U.S. Appl. No. 10/264,306, Mail Date Jun. 27, 2008, Office Action.
U.S. Appl. No. 11/198,811, Mail Date Aug. 26, 2008, Office Action.
U.S. Appl. No. 12/113,092, filed Apr. 30, 2008, Ginn et al.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 10/435,104, Mail Date Nov. 14, 2007, Notice of Allowance.
U.S. Appl. No. 10/541,083, Mail Date Oct. 31, 2007, Office Action.
U.S. Appl. No. 10/682,459, Mail Date Dec. 4, 2008, Office Action.
U.S. Appl. No. 10/908,721, Mail Date Nov. 25, 2008, Office Action.
U.S. Appl. No. 11/744,089, Mail Date Nov. 26, 2008, Office Action.
McCarthy, et al., "Tension (Stay) Suture Bridge", J. of International College of Surgeons, 34(5), pp. 613-614 (Nov. 1960).
U.S. Appl. No. 10/305,923, Mail Date Nov. 1, 2004, Office Action.
U.S. Appl. No. 10/305,923, Mail Date Mar. 3, 2005, Notice of Allowance.
U.S. Appl. No. 10/356,214, Mail Date Nov. 4, 2008, Office Action.
U.S. Appl. No. 11/461,323, Mail Date May 2, 2007, Office Action.
U.S. Appl. No. 11/461,323, Mail Date Oct. 29, 2007, Office Action.
U.S. Appl. No. 11/461,323, Mail Date Apr. 25, 2008, Office Action.
U.S. Appl. No. 11/461,323, Mail Date Nov. 6, 2008, Office Action.
U.S. Appl. No. 10/517,004, Mail Date Aug. 13, 2008, Notice of Allowance.
U.S. Appl. No. 10/638,115, Mail Date Oct. 29, 2008, Office Action.
U.S. Appl. No. 10/786,444, Mail Date Oct. 17, 2008, Office Action.
U.S. Appl. No. 10/787,073, Mail Date Nov. 12, 2008, Office Action.
U.S. Appl. No. 10/435,104, Mail Date Dec. 22, 2008, Supplemental Notice of Allowability.
U.S. Appl. No. 10/541,083, Mail Date Dec. 29, 2008, Notice of Allowance.
U.S. Appl. No. 11/344,891, Mail Date Dec. 8, 2008, Office Action.
U.S. Appl. No. 60/696,096, filed Jul. 1, 2005, Pantages et al.
U.S. Appl. No. 60/946,026, filed Jun. 25, 2007, Ellingwood.
U.S. Appl. No. 10/006,400, Mail Date Jan. 2, 2009, Office Action.
U.S. Appl. No. 11/152,562, Mail Date Feb. 13, 2009, Office Action.
U.S. Appl. No. 11/344,793, Mail Date Jan. 22, 2009, Office Action.
U.S. Appl. No. 11/396,731, Mail Date Feb. 13, 2009, Office Action.
U.S. Appl. No. 11/411,925, Mail Date Jan. 12, 2009, Office Action.
U.S. Appl. No. 11/427,297, Mail Date Jan. 30, 2009, Office Action.
U.S. Appl. No. 12/106,928, Mail Date Jan. 23, 2009, Office Action.
U.S. Appl. No. 09/680,837, Mailed Date Jul. 9, 2002, Office Action.
U.S. Appl. No. 09/680,837, Mail Date Nov. 6, 2002, Office Action.
U.S. Appl. No. 09/680,837, Mail Date Mar. 25, 2003, Office Action.
U.S. Appl. No. 09/680,837, Mail Date Jun. 16, 2003, Notice of Allowance.
U.S. Appl. No. 09/680,837, Mail Date Sep. 11, 2003, Issue Notification.
U.S. Appl. No. 10/147,774, Mail Date Mar. 18, 2009, Office Action.
U.S. Appl. No. 10/264,306, Mail Date Feb. 26, 2009, Office Action.
U.S. Appl. No. 10/356,214, Mail Date Apr. 29, 2009, Office Action.
U.S. Appl. No. 10/667,144, Mail Date Mar. 24, 2009, Office Action.
U.S. Appl. No. 10/669,313, Mail Date Oct. 31, 2005, Office Action.
U.S. Appl. No. 10/669,313, Mail Date Jan. 11, 2006, Notice of Allowance.
U.S. Appl. No. 10/669,313, Mail Date Jun. 28, 2006, Notice of Allowance.

U.S. Appl. No. 10/669,313, Mail Date Nov. 15, 2006, Issue Notification.
U.S. Appl. No. 11/048,503, Mail Date Mar. 13, 2009, Office Action.
U.S. Appl. No. 11/344,868, Mail Date Mar. 25, 2009, Office Action.
U.S. Appl. No. 11/344,891, Mail Date Feb. 26, 2009, Office Action.
U.S. Appl. No. 11/406,203, Mail Date Mar. 3, 2009, Office Action.
U.S. Appl. No. 11/532,325, Mail Date Feb. 23, 2009, Office Action.
U.S. Appl. No. 12/106,937, Mail Date Mar. 30, 2009, Office Action.
U.S. Appl. No. 29/296,370, Mail Date Aug. 18, 2008, Office Action.
U.S. Appl. No. 29/296,370, Mail Date Dec. 2, 2008, Notice of Allowance.
U.S. Appl. No. 29/296,370, Mail Date Apr. 1, 2009, Notice of Allowance.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
U.S. Appl. No. 10/638,115, filed May 7, 2009, Notice of Allowance.
U.S. Appl. No. 11/396141, filed May 22, 2009, Office Action.
U.S. Appl. No. 11/396731, filed. May 22, 2009, Office Action.
U.S. Appl. No. 10/006,400, filed Jul. 9, 2009, Notice of Allowance.
U.S. Appl. No. 10/027,681, filed Jul. 8, 2009, Office Action.
U.S. Appl. No. 10/264,306, filed Aug. 13, 2009, Office Action.
U.S. Appl. No. 10/541,083, filed Apr. 16, 2009, Notice of Allowance.
U.S. Appl. No. 10/616,832, filed Jul. 21, 2009, Office Action.
U.S. Appl. No. 10/682,459, filed Jun. 10, 2009, Office Action.
U.S. Appl. No. 10/786,444, filed. Jun. 18, 2009, Office Action.
U.S. Appl. No. 10/787,073, filed. Aug. 13, 2009, Office Action.
U.S. Appl. No. 10/908,721, filed. Jun. 23, 2009, Office Action.
U.S. Appl. No. 11/048,503, filed. Jun. 26, 2009, Office Action.
U.S. Appl. No. 11/113,549, filed. Jul. 21, 2009, Office Action.
U.S. Appl. No. 11/152,562, filed Jul. 6, 2009, Office Action.
U.S. Appl. No. 11/390,586, filed. Jun. 24, 2009, Office Action.
U.S. Appl. No. 11/396,141, filed Aug. 26, 2009, Office Action.
U.S. Appl. No. 11/461,323, filed Jul. 27, 2009, Office Action.
U.S. Appl. No. 11/532,325, filed Jun. 17, 2009, Office Action.
U.S. Appl. No. 11/744,089, filed Aug. 14, 2009, Office Action.
U.S. Appl. No. 10/147,774, filed Oct. 26, 2009, Office Action.
U.S. Appl. No. 10/541,083, filed Sep. 30, 2009, Notice of Allowance.
U.S. Appl. No. 10/667,144, filed Nov. 23, 2009, Office Action.
U.S. Appl. No. 11/198,811, filed Sep. 22, 2009, Office Action.
U.S. Appl. No. 11/344,891, filed Oct. 7, 2009, Office Action.
U.S. Appl. No. 11/406,203, filed Sep. 16, 2009, Office Action.
U.S. Appl. No. 11/411, 925, filed Sep. 10, 2009, Office Action.
U.S. Appl. No. 11/427, 297, filed Sep. 15, 2009, Office Action.
U.S. Appl. No. 11/958, 295, filed Aug. 27, 2009, Office Action.
U.S. Appl. No. 12/106, 937, filed Nov. 18, 2009, Office Action.
U.S. Appl. No. 12/106, 928, filed Oct. 5, 2009, Office Action.
U.S. Appl. No. 12/403,256, filed Dec. 16, 2009, Restriction Requirement.
Marshall A.C., Lock J.E., Structural and Compliant Anatomy of the Patent Foramen Ovale in Patients Undergoing Transcatheter Closure, Am Heart J 2000 Aug.; 140(2); pp. 303-307.
Taber's Cyclopedic Medical Dictionary, 18th Ed. 1997, pp. 747 and 1420.
U.S. Appl. No. 10/006,400, filed Jan. 13, 2010, Notice of Allowance.
U.S. Appl. No. 10/264,306, filed Jan. 27, 2010, Office Action.
U.S. Appl. No. 10/356,214, filed Jan. 13, 2010, Notice of Allowance.
U.S. Appl. No. 10/435,104, filed Jan. 20, 2010, Notice of Allowance.
U.S. Appl. No. 10/541,083, filed Feb. 5, 2010, Notice of Allowance.
U.S. Appl. No. 10/616,832, filed Jan. 11, 2010, Notice of Allowance.
U.S. Appl. No. 10/638,115, filed Dec. 1, 2009, Notice of Allowance.
U.S. Appl. No. 10/682,459, filed Dec. 23, 2009, Office Action.
U.S. Appl. No. 10/786,444, filed Jan. 14, 2010, Office Action.
U.S. Appl. No. 10/787,073, filed Feb. 17, 2010, Notice of Allowance.
U.S. Appl. No. 10/908,721, filed Feb. 2, 2010, Office Action.
U.S. Appl. No. 11/048,503, filed Jan. 11, 2010, Notice of Allowance.
U.S. Appl. No. 11/455,993, filed Feb. 17, 2009, Office Action.
U.S. Appl. No. 11/455,993, filed Dec. 16, 2009, Office Action.
U.S. Appl. No. 11/532,325, filed Jan. 5, 2010, Office Action.
U.S. Appl. No. 11/532,576, filed Mar. 1, 2010, Office Action.
U.S. Appl. No. 11/675,462, filed Dec. 10, 2009, Office Action.
U.S. Appl. No. 11/767,818, filed Dec. 24, 2009, Office Action.
U.S. Appl. No. 11/767,818, filed Mar. 22, 2010, Office Action.
U.S. Appl. No. 11/959,334, filed Aug. 19, 2009, Office Action.
U.S. Appl. No. 11/959,334, filed Jan. 12, 2010, Notice of Allowance.
U.S. Appl. No. 12/402,398, filed Mar. 9, 2010, Office Action.
U.S. Appl. No. 29/296,370, filed, Feb. 10, 2010, Issue Notification.
U.S. Appl. No. 10/638,115, filed Apr. 2, 2010, Notice of Allowance.
U.S. Appl. No. 11/461,323, filed Apr. 5, 2010, Notice of Allowance.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 61/097,072, filed Sep. 15, 2008, Sibbitt Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
U.S. Appl. No. 10/006,400, filed Apr. 27, 2010, Notice of Allowance.
U.S. Appl. No. 10/147,774, filed Jun. 8, 2010, Office Action.
U.S. Appl. No. 10/264,306, filed Jun. 15, 2010, Office Action.
U.S. Appl. No. 10/356,214, filed May 13, 2010, Notice of Allowance.
U.S. Appl. No. 10/435,104, filed Jun. 2, 2010, Office Action.
U.S. Appl. No. 10/541,083, filed May 10, 2010, Notice of Allowance.
U.S. Appl. No. 10/616,832, filed May 12, 2010, Notice of Allowance.
U.S. Appl. No. 10/667,144, filed Jun. 22, 2010, Office Action.
U.S. Appl. No. 10/682,459, filed Apr. 28, 2010, Office Action.
U.S. Appl. No. 11/048,503, filed Apr. 26, 2010, Notice of Allowance.
U.S. Appl. No. 11/113,549, filed Jul. 6, 2010, Office Action.
U.S. Appl. No. 11/152,562, filed Mar. 31, 2010, Office Action.
U.S. Appl. No. 11/198,811, filed Jun. 29, 2010, Notice of Allowance.
U.S. Appl. No. 11/316,775, filed Apr. 16, 2008, Office Action.
U.S. Appl. No. 11/316,775, filed Aug. 6, 2008, Office Action.
U.S. Appl. No. 11/344,891, filed May 7, 2010, Office Action.
U.S. Appl. No. 11/390,586, filed Jul. 6, 2010, Office Action.
U.S. Appl. No. 11/396,141, filed May 4, 2010, Office Action.
U.S. Appl. No. 11/396,731, filed Jun. 29, 2010, Office Action.
U.S. Appl. No. 11/406,203, filed Jun. 18, 2010, Notice of Allowance.
U.S. Appl. No. 11/508,656, filed Dec. 9, 2009, Office Action.
U.S. Appl. No. 11/508,656, filed Mar. 25, 2010, Office Action.
U.S. Appl. No. 11/508,662, filed Dec. 28, 2009, Office Action.
U.S. Appl. No. 11/508,662, filed Apr. 14, 2010, Office Action.
U.S. Appl. No. 11/532,576, filed Apr. 23, 2010, Office Action.
U.S. Appl. No. 11/674,930, filed Jan. 8, 2009, Office Action.
U.S. Appl. No. 11/674,930, filed Jun. 4, 2009, Office Action.
U.S. Appl. No. 11/674,930, filed Jan. 8, 2010, Office Action.
U.S. Appl. No. 11/852,190, filed Jun. 24, 2010, Office Action.
U.S. Appl. No. 11/958,295, filed May 25, 2010, Office Action.
U.S. Appl. No. 11/959,334, filed Apr. 14, 2010, Notice of Allowance.
U.S. Appl. No. 12/106,928, filed May 10, 2010, Office Action.
U.S. Appl. No. 12/113,851, filed Apr. 27, 2010, Office Action.
U.S. Appl. No. 12/113,851, filed Jun. 24, 2010, Office Action.
U.S. Appl. No. 12/402,398, filed May 20, 2010, Office Action.
U.S. Appl. No. 12/403,256, filed Mar. 30, 2010, Office Action.
U.S. Appl. No. 12/403,277, filed Jul. 8, 2010, Office Action.
U.S. Appl. No. 10/435,104, filed Jul. 23, 2009, Notice of Allowance.
U.S. Appl. No. 10/669,313, filed Oct. 31, 2005, Office Action.
U.S. Appl. No. 11/508,715, filed Jan. 6, 2010, Office Action.
U.S. Appl. No. 11/508,715, filed Apr. 26, 2010, Office Action.
U.S. Appl. No. 11/959,334, filed Jul. 23, 2010, Notice of Allowance.

* cited by examiner

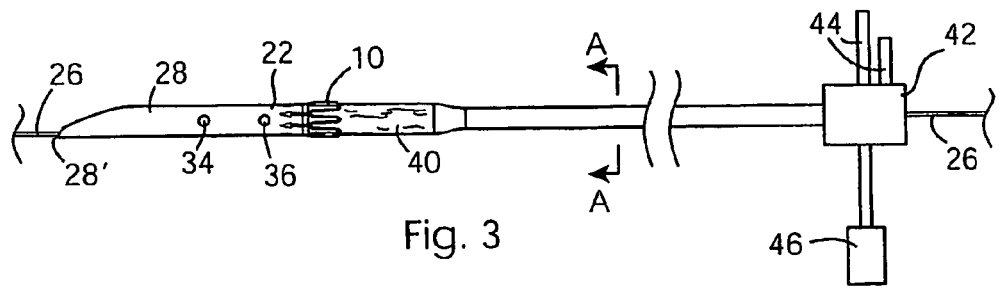
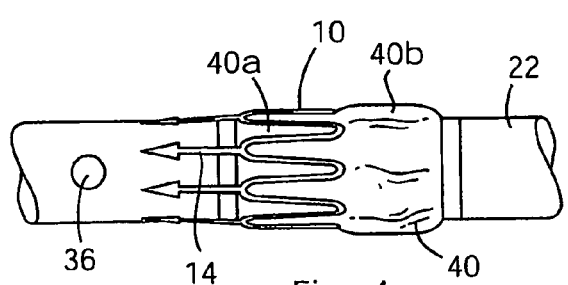
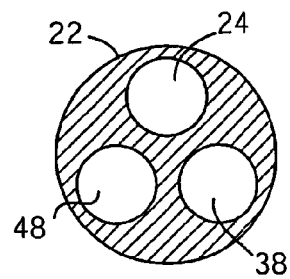
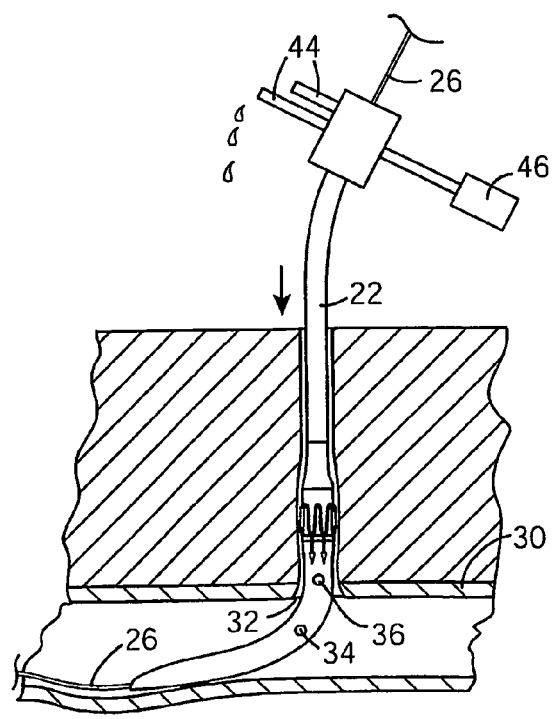
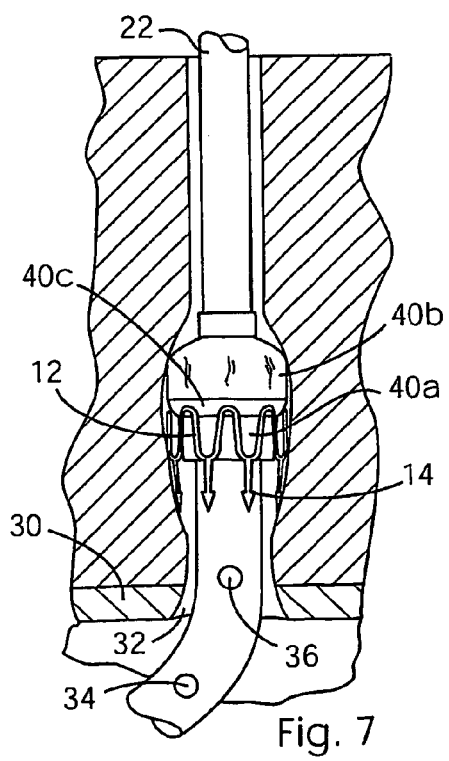

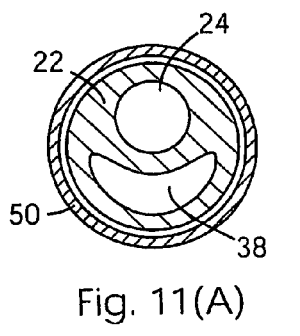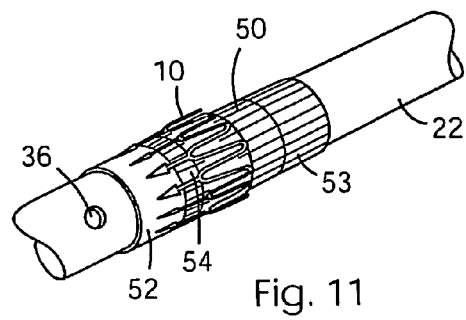
Fig. 11(A)  Fig. 11
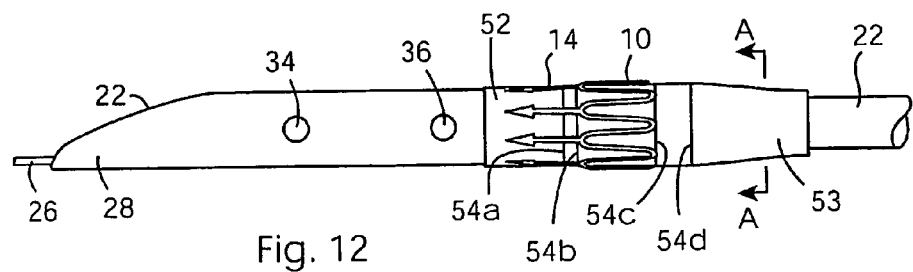
Fig. 12
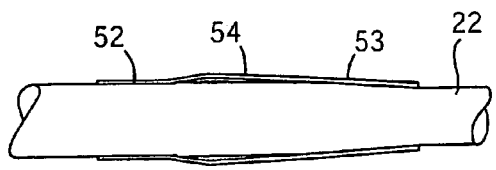
(a)
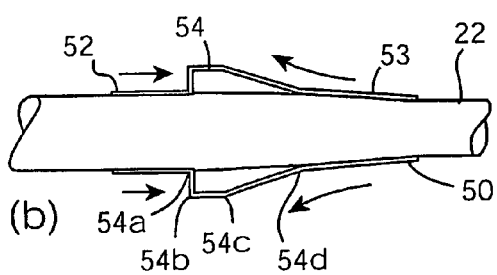
(b)
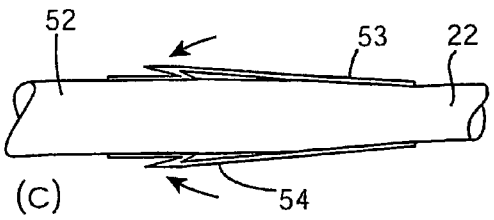
Fig. 13 (c)

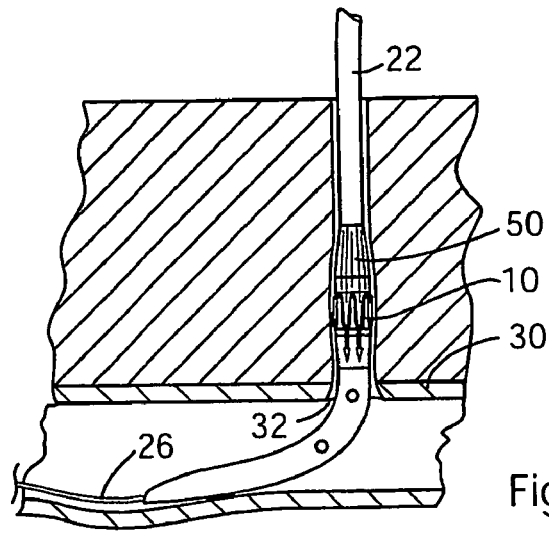
Fig. 14
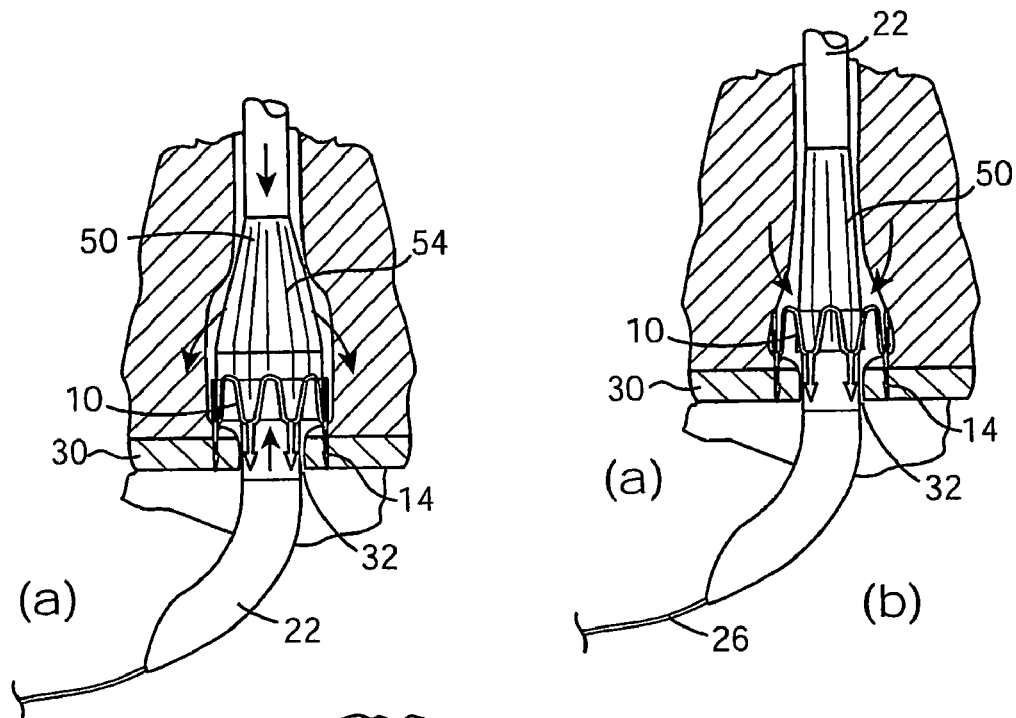
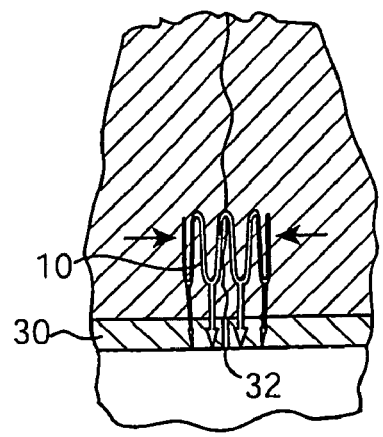
Fig. 15

BLOOD VESSEL CLOSURE CLIP AND DELIVERY DEVICE

This application is a 371 of PCT/IE03/00088, filed on Jun. 4, 2003.

FIELD OF THE INVENTION

This invention relates to a clip for closing a puncture hole in a blood vessel, and to a device for closing a puncture hole using such a clip.

BACKGROUND

Numerous medical diagnostic and interventional procedures involve the use of long catheters which are placed within the human vascular system. These catheters are delivered over guide wires to positions in the heart for cardiac procedures and into the brain for neurological procedures. The point of entry is normally a puncture hole in the femoral artery in the patient's groin. Once the procedure has been completed the catheter and guide wire are removed and the puncture hole must be closed in order to prevent excessive bleeding and the possibility of infection. Traditionally this puncture hole has been closed by maintaining manual pressure at the puncture site until homeostasis occurs around the puncture hole or placing sand bags on an area of the groin close to the puncture hole and keeping the patient immobilised until homeostasis occurs.

In recent times a number of medical devices have been developed and marketed for the purpose of closing this puncture hole. These devices fall broadly into two categories (a) mechanical closure devices such as those which use sutures or staples to mechanically close the puncture hole, and (b) occlusion devices such as collagen plugs and gels. Examples of prior art in this area include U.S. Pat. Nos. 5,860,991 and 6,322,580.

U.S. Pat. No. 5,860,991 describes a device for closing puncture holes utilizing a suture. The device is positioned into the artery over the guide wire until a blood signal appears at the proximal end indicating proper position has been attained. At this point an internal anchor is deployed and needles are advanced from outside the artery, through the arterial wall and into the anchor component to grab opposite ends of a suture loop. The needles are then retracted back into the device and the device is removed from the artery leaving the open ends of the suture external on the patients skin. A knot is tied and run down the suture tightening the loop around the puncture hole and closing it. A cutter device is then used to cut the suture.

The problems associated with this device are the significant number of steps in its use, tying of the suture loop involves a sawing action around the puncture hole which could unintentionally cause the suture to cut its way through the hole, pushing needles from outside the artery to inside creates two additional puncture holes and finally a loop of suture remains inside the artery and has the potential to dislodge plaque within the artery.

Another example of a mechanical closure device is described in U.S. Pat. No. 6,322,580 which uses a metallic staple to close the puncture hole. This device involves the use of a special dilator and sheath which are guided into the femoral artery over a guide wire. Once the guide wire is removed internal stabilizers are activated and retracted against the internal wall of the artery. The sheath dilator is then removed and a stapler device is advanced through the sheath and the staple deployed into the arterial wall. The stapler is then removed, the stabilisers deactivated and the introducer sheath removed from the tissue tract.

Problems associated with this device include the use of a specialised sheath which must be inserted over the guide wire and advanced into the tissue tract before the closure procedure can take place. In addition delicate stabiliser type devices must be deployed within the artery before the stapler can be delivered to close the puncture hole. Once the staple is delivered the staple device is removed from the sheath, the internal stabilisers are then collapsed and retracted through the puncture hole and into the sheath before the sheath itself can be removed from the tissue tract.

While both devices described above are effective in terms of closing puncture holes they are mechanically complex in nature in terms of operation. In addition a significant number of steps are involved in the procedure. The end users of such devices are more familiar with catheter-based technologies delivered over guide wires, combined with the inflation and deflation of balloons. Therefore there is a need for an improved puncture closure device which operates in a manner more consistent with catheter based devices such as angiography and angioplasty catheters. In addition there is a need to reduce the complexity of such devices by reducing the number of components involved and the number of steps involved in the procedure.

SUMMARY OF THE INVENTION

Accordingly, the present invention provides a clip for closing a puncture hole in a blood vessel, the clip comprising a ring having a resiliently expandable circumference and a plurality of barbed prongs extending at least approximately in the same direction from one edge of the ring.

The ring may be circular or any suitable closed-loop shape.

The invention further provides a device for closing a puncture hole in a blood vessel using a clip of the kind aforesaid, the apparatus comprising an elongated body having a front end for insertion through the hole into the blood vessel and a clip expander positioned on the body rearwardly of the front end for receiving the clip with its ring surrounding the expander and its prongs projecting towards the front end of the body, the clip expander being actuable to resiliently expand the circumference of the ring, the clip being movable forwardly in its expanded state so that the prongs pierce the tissue around the hole, and the clip expander thereafter being actuable to release the clip so that the body and clip expander can be withdrawn from the ring.

In one embodiment the clip, herein referred to as a "ring occluder", is placed over a deflated balloon which in turn is bonded to the shaft of a plastics catheter. Inflation of the balloon exerts an outward expanding force under the ring occluder causing it to expand to a diameter equivalent to a fully expanded diameter of the balloon on which it sits. Barbed legs extend from one edge of the occluder ring for a distance of 3-5 mm. The catheter has three lumen, one provides a channel for liquid to inflate the balloon, one is a channel for blood and the third channel accommodates the guide wire.

In clinical use the catheter is positioned on the guide wire and delivered over the guide wire through the tissue tract and into the blood vessel. The catheter is advanced until a blood signal appears at the blood back port. This indicates that the blood entry port is now positioned within the blood vessel. The catheter is now retracted until blood flow stops indicating that the blood entry port is now positioned within the puncture hole and the ring occluder is positioned a pre-determined distance form the wall of the blood vessel. The guide wire may now be removed. The balloon is then inflated using saline solution which in turn causes the ring occluder to increase in diameter and expand outward into the tissue tract. The diameter of the balloon on the rear side of the ring occluder is greater in diameter so as to provide a shoulder or edge to advance the ring occluder forward. Once fully expanded the catheter is pushed forward causing the barbed legs of the ring occluder to penetrate the surrounding tissue and arterial wall in the proximity of the puncture hole. The catheter continues to advance until significant forward resistance is met. This indicates to the user that the catheter should not be advanced any further as the barbed legs should now be positioned within the arterial wall. The expanding balloon is then deflated, the guide wire removed from the catheter and the catheter removed from the tissue tract. On removal of the catheter the recoiling force of the ring occluder will pull the edges of the puncture hole together thereby sealing the hole closed.

In another embodiment the balloon is replaced by a sliding collar which has splines which are forced mutually outwards to deform the ring occluder.

The advantage of such devices are that they are significantly simpler to operate than previously described mechanical closure devices. In addition, the mode of operation of the balloon device is consistent with that of other devices used by interventional radiologists and cardiologists in that it provides a catheter delivered over a guide wire with a balloon which is inflated from an external port.

BRIEF DESCRIPTION OF THE DRAWINGS

Embodiments on the invention will now be described, by way of example, with reference to the accompanying drawings, in which:

FIG. 3 is a plan view of a first embodiment of catheter delivery device for the ring occluder of FIG. 1 or FIG. 2.

FIG. 4 is an enlarged view of the delivery device of FIG. 3 in the region of the ring occluder and inflatable balloon.

FIG. 5 is a cross sectional view of the catheter on the plane A-A of FIG. 3.

FIGS. 6-10 illustrate successive stages of the catheter delivery device in use.

FIG. 11 is a perspective view of a second embodiment of catheter delivery device in a non-expanded condition.

FIG. 11(A) is a cross sectional view of the second embodiment of catheter on the plane A-A of FIG. 12.

FIG. 12 is an elevational view of the device shown in FIG. 11.

FIG. 13(A) is an elevational view of the ring occluder deployment means (expander) of the second embodiment of catheter delivery device in its initial rest position.

FIG. 13(B) is an elevational view of the expander of FIG. 13(A) in its mid-forward and fully expanded state.

FIG. 13(C) is an elevational view of the expander of FIG. 13(A) in its fully forward and collapsed state.

FIGS. 14 and 15 illustrate successive stages of the second embodiment of catheter delivery device in use.

DETAILED DESCRIPTION OF THE INVENTION

Figure 1:
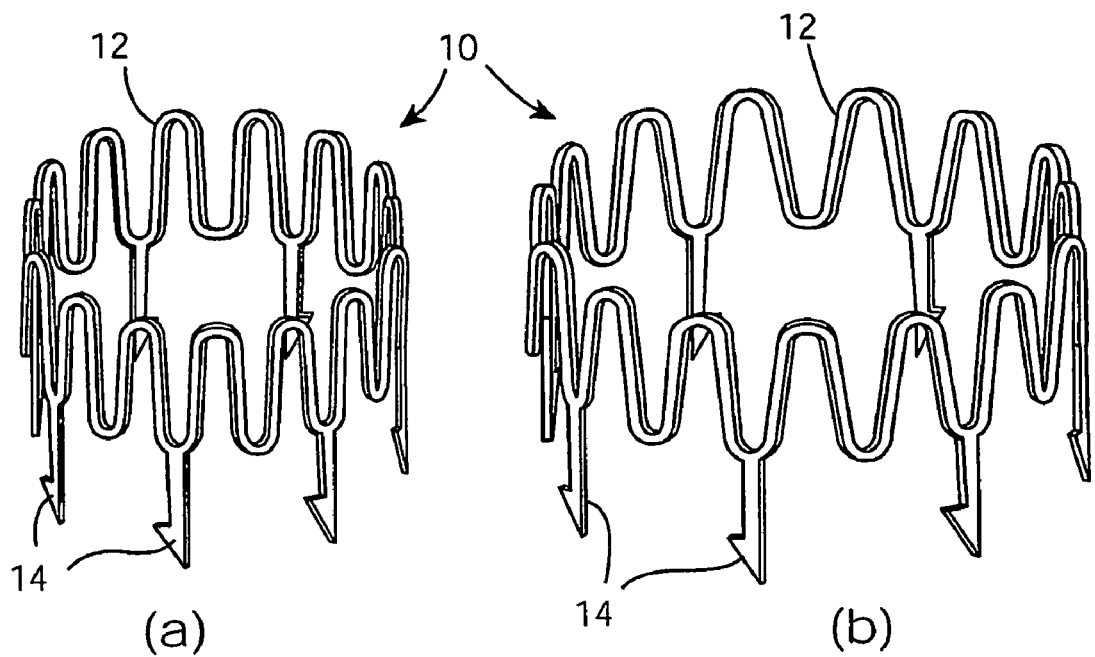
FIG. 1 is a perspective view of one embodiment of a ring occluder according to the invention in both its unexpanded and expanded conditions.

Referring first to FIG. 1, a ring occluder 10 for closing a puncture hole in a blood vessel comprises a circumferentially continuous metal ring 12. The circumference of the ring 12 is sinuous and the ring has a plurality of sharp metal prongs 14 extending at least approximately in the same direction from one edge (in FIG. 1 the lower edge) of the ring 12. The prongs are 3-5 mm in length and extend from alternate minima of the sinuous shape. The prongs 14 are barbed, meaning in the present context that they are configured to resist withdrawal once they penetrate tissue. The prongs 14 preferably mutually converge slightly towards the centre axis of the ring 12. FIG. 1(a) shows the ring occluder in its non-expanded state, while FIG. 1(b) shows the ring occluder in its expanded state where the pitch between the peaks of the sinuous configuration have been increased in a manner which provides uniform expansion of the ring at all points on its circumference. The pitch between the barbed prongs increases accordingly.

Figure 2:
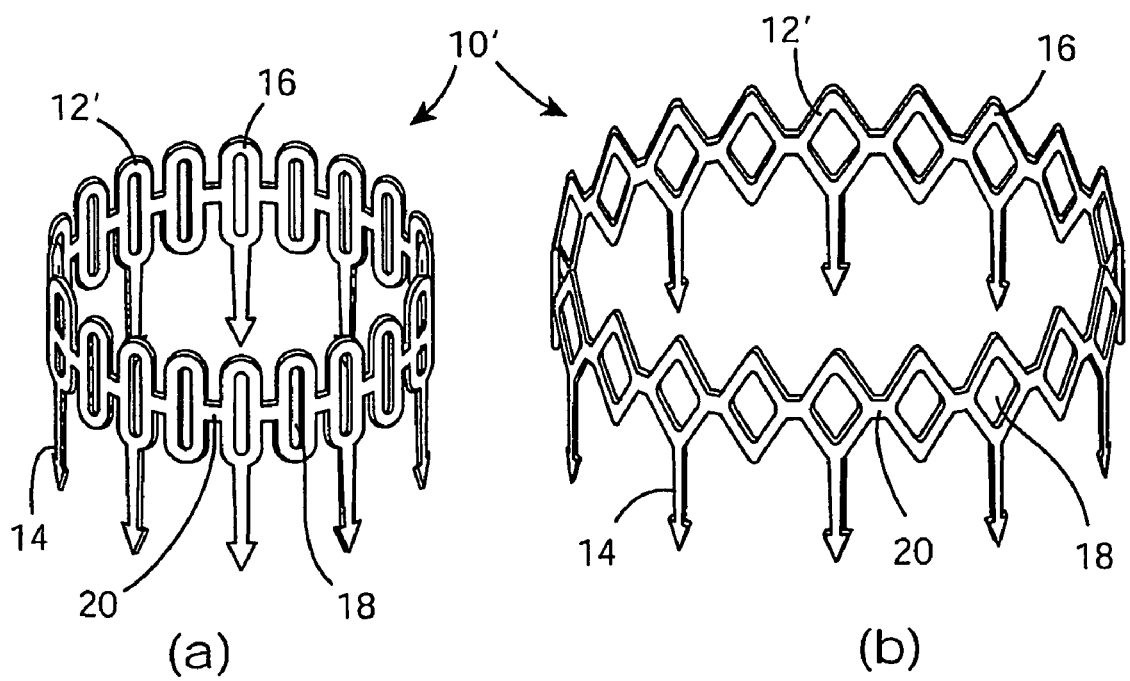
FIG. 2 is a perspective view of a second embodiment of a ring occluder in its unexpanded and expanded conditions.

FIG. 2(a) shows an alternative embodiment of ring occluder 10' in its non-expanded state. In this case the circumference of the ring 12' is made up of a plurality of oval-shaped segments 16 each with a longitudinal central slit 18. The oval segments 16 are disposed side-by-side round the ring 12 with their longitudinal axes substantially parallel. Each oval segment 16 is joined to the next by a narrow central waist 20. On expansion of the ring as illustrated in FIG. 2(b) the oval segments expand to a more round or open configuration therefore increasing the overall diameter of the ring 12 and the pitch between the barbed legs 14 which extend from the base of every second oval segment.

In both cases the material used to fabricate the ring occluders 10 and 10' is such that permanent metal deformation does not occur on expansion of the occluder from its non-expanded state to its expanded state. The force exerted on the occluders is such that they remain within the elastic range of the material used thereby ensuring that when the expanding force is removed the occluder returns resiliently to its non-expanded state. Preferably the diameter of the ring 12 can be resiliently increased by a factor of three with return substantially to its original diameter upon removal of the expanding force. An example of a suitable material for making the occluder is Nitinol or Memory Metal.

FIGS. 3 to 5 show a first embodiment of catheter delivery device with a ring occluder 10 in position (the device could just as well be used with the ring occluder 10'). The catheter 22 is a flexible, elongated plastics body having a longitudinal bore 24 (FIG. 5) by which the catheter can be slid along a pre-positioned guide wire 26. The front end 28 of the catheter 22 is tapered down onto the guide wire 26 which guides it into position within the blood vessel 30, FIG. 6, through a hole 32 in the sidewall of the blood vessel. Between the front end 28 and the ring occluder 10 is a blood entry port 34. The port 34 allows blood to enter a further longitudinal bore 38 in the catheter 22. An inflatable enclosure ("balloon") 40 is positioned on the catheter 22 approximately 5 cm to the rear of the extreme forward tip 28' of the front end 28. The balloon 40 coaxially surrounds the catheter and in its deflated state lies tightly against the catheter body. The ring occluder 10 is positioned on the balloon 40 toward its forward end, the ring 12 coaxially surrounding the balloon and catheter. A hub 42 is positioned at the rear end of the catheter 22 from which extends a blood port 44 connected to bore 38 within the catheter, which in turn is connected to blood entry port 34. In addition, there is a balloon inflation port 46 connected to a further longitudinal bore 48 in the catheter 22, the bore 48 communicating with the interior of the balloon 40. The port 46 allows fluid under pressure (such as a saline solution) to be delivered into the balloon 40 to inflate it, and also allows fluid in the balloon to be vented to allow it to revert to its deflated state.

FIG. 4 is a view of the device in the region of the ring occluder 10. The balloon 40 is formed with two axially adjacent regions 40a, 40b such that when the balloon is inflated these regions have different diameters, FIG. 7. In particular, when the balloon is inflated the front region 40a, around which the occluder 10 is positioned, has a lesser diameter than the adjacent rear region 40b. The reason for this is to provide a shoulder 40c behind the ring 12 with which the ring occluder 10 can be pushed forward into the tissue surrounding the puncture hole 32 by pushing the catheter 22 as a whole in a forward direction. Only the ring 22 is positioned on the balloon 40. The barbed prongs 14 extend freely in a forward direction and converge slightly towards the catheter body. In order to ensure that, when the balloon is inflated, the region 40b does not expand at the expense of the region 40a, the region 40b and shoulder 40c are made of a thicker material than the region 40a.

Figure 8:
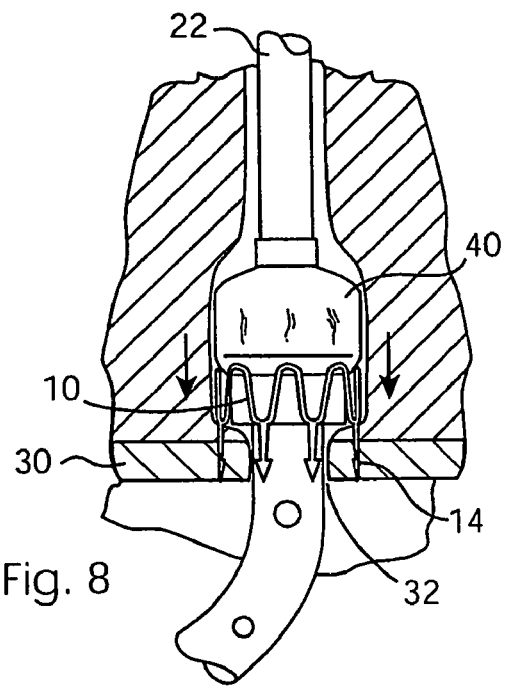
Figure 9:
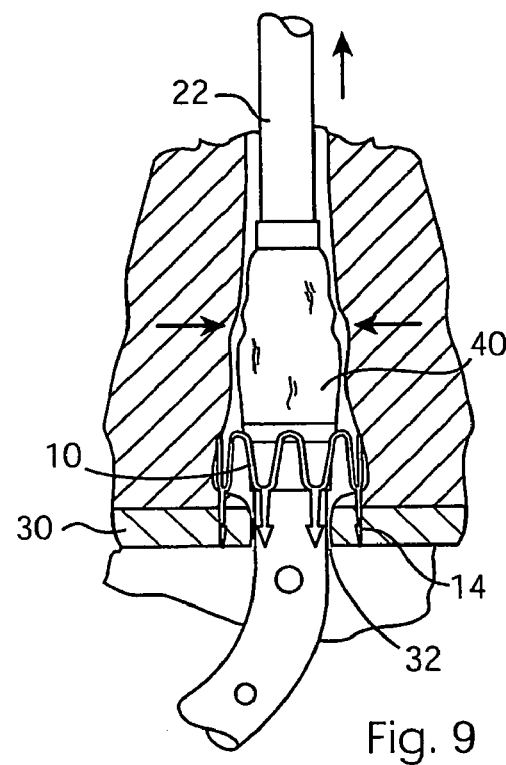
Figure 10:
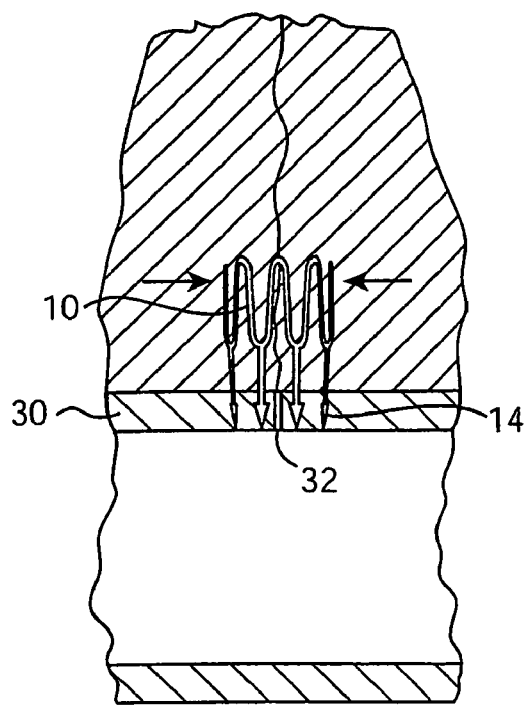

FIGS. 6 to 10 illustrate the device in clinical use. Referring first to FIG. 6, the catheter 22 is positioned on the guide wire 26 and slid forwardly thereon through the tissue tract until the front end 28 of the catheter enters the blood vessel 30. The catheter 22 is advanced forward until the blood entry port 34 enters the blood vessel indicated by blood flowing from the blood back port 44. Advancement of the catheter is stopped and the balloon 40 is then inflated, as illustrated in FIG. 7, by fluid pressure applied at the port 46. Inflation of the balloon causes the ring occluder 10 to resiliently expand. Once fully expanded the catheter 22 is advanced forwardly as shown in FIG. 8. In doing so the shoulder 40c on the balloon 40 pushes against the ring occluder 10 causing the prongs 14 to penetrating overlying tissue and the arterial wall. The catheter 22 is advanced until significant resistance prevents any further advancement. This indicates proper position of the ring occluder 10. Now the balloon 40 is fully deflated by venting through the port 46 resulting in some resilient contraction of the ring occluder 10 around the catheter 22 as illustrated in FIG. 9. Once fully deflated the guide wire 26 and catheter 22 are removed from the tissue tract and the puncture hole 32 causing the ring occluder 10 to resiliently contract to its initial state thereby pulling the edges of the puncture hole 32 together and effecting homeostasis. The closed ring occluder 10 remains positioned around the puncture hole on the artery as illustrated in FIG. 10.

Although the foregoing has shown the ring 12 or 12' as circular, and the balloon 40 circularly symmetric around the catheter 22, the ring does not need to be circular but can be any closed-loop shape as dictated by the cross-section of the balloon which can also vary. The term "ring" is to be interpreted accordingly.

FIGS. 11 to 13 show an alternative embodiment of a catheter delivery device for the ring occluder 10 or 10'. In place of the balloon 40 used in the previous embodiment, a mechanical expander is used; otherwise, all features of the previous embodiment may be present in the current embodiment. The mechanical expander comprises an oversleeve 50 on the catheter 22. FIG. 11(A) shows a cross-section through the catheter in the region of the oversleeve 50. The catheter has a longitudinal guide wire bore 24 and blood return bore 38 as previously described, and the sleeve 50 is seen coaxially surrounding the catheter body. The forward end 52 of the sleeve is fixed to the outer surface of the catheter, while the rear end 53 of the sleeve 50 is slidable on the catheter 22. A section of the sleeve 50 intermediate its ends, onto which the occluder is mounted in use, is slit longitudinally to form a series of spines 54. Each spline 54 has four hinge points 54a, 54b, 54c and 54d, the hinge points 54a and 54d being at the front and rear ends of the spline and the hinge points 54b and 54c being intermediate them. The two intermediate hinge points 54b, 54c generally align with the upper and lower edges respectively of the expandable ring 12 section of the occluder 10 as illustrated in FIG. 12.

In the unexpanded state as shown in FIG. 13(a) the splines 54 lie flush with the catheter. If the rear end 53 of the sleeve 50 is slid along the catheter 22 towards the fixed front end 52 the splines 54 are forced mutually radially outwardly as shown in FIG. 13(b) thus resiliently expanding the occluder 10 and at the same time advancing it in a forward direction. With continued advancement of the rear end 53 of the sleeve the splines collapse mutually inwardly down onto the catheter thus releasing the occluder 10 from the splined section.

In clinical use the catheter 22 is slid over a guide wire 26 as shown in FIG. 14 until a blood signal is received at the port 44 thus indicating proper positioning. At this point the rear end 53 of the sleeve 50 is advanced causing the occluder 10 to resiliently expand and simultaneously advance to stab the wall 30 of the artery, FIG. 15(a). As the rear end 53 of the sleeve is advanced further it releases the occluder 10, FIG. 15(b), so that the catheter and guide wire can be retracted from the puncture hole 32 allowing the occluder 10 to fully contract and close the puncture hole, FIG. 15(c).

The invention is not limited to the embodiments described herein which may be modified or varied without departing from the scope of the invention.

The invention claimed is:

1. A device for closing a puncture hole in a blood vessel, comprising:
    an elongated body having a front end for insertion through the hole into the blood vessel;
    a clip expander positioned on the body rearwardly of the front end, the clip expander comprises a sleeve surrounding the body which has one end fixed relative to the body, a section of the sleeve intermediate its ends being slit longitudinally to form a plurality of splines which can be forced mutually outwardly by sliding the other end of the sleeve along the body towards the fixed end of the sleeve;
    a clip having a ring disposed around the expander and prongs projecting towards the front end of the body, the clip being mounted on the splined section of the sleeve; and
    wherein the clip expander is actuable to resiliently expand the circumference of the ring, the clip being movable forwardly in its expanded state so that the prongs pierce the tissue around the hole, and the clip expander thereafter being actuable to release the clip so that the body and clip expander can be withdrawn from the ring.

2. The device of claim 1, wherein the prongs converge slightly towards the center of the ring.

3. The device of claim 1, wherein the ring is sinuous.

4. The device of claim 1, wherein the ring comprises a plurality of elongated segments each with a longitudinal center slit, the segments being disposed side by side around the ring with their longitudinal axes substantially parallel and being joined each to the next by a relatively narrow waist.

5. The device of claim 1, wherein the body has a longitudinal bore to slidably accommodate a guide wire pre-positioned at the puncture hole.

6. The device of claim 1, wherein the body has a longitudinal bore to serve as a blood return channel.

7. The device of claim 1, wherein the splines are hinged such that as the splines move mutually outwardly to expand the ring they also advance the clip towards the forward end of the body.

8. The device of claim 7, wherein after advancing the clip, further movement of the said other end of the sleeve towards the fixed end moves the splines mutually inwardly to release the clip.

* * * * *